(12) United States Patent
Hatake et al.

(10) Patent No.: US 7,419,667 B2
(45) Date of Patent: Sep. 2, 2008

(54) DRUG FOR CANCER THERAPY

(75) Inventors: Kiyohiko Hatake, Tokyo (JP); Yasuhito Terui, Tokyo (JP); Yuji Mishima, Tokyo (JP); Akio Yamada, Zama (JP); Takuma Sakurai, Zama (JP); Takehito Itoh, Zama (JP)

(73) Assignee: Morinaga Milk Industry Co. Ltd., Minato-ku, Tokyo (JP)

( * ) Notice: Subject to any disclaimer, the term of this patent is extended or adjusted under 35 U.S.C. 154(b) by 170 days.

(21) Appl. No.: 10/564,302

(22) PCT Filed: Mar. 9, 2005

(86) PCT No.: PCT/JP2005/004123

§ 371 (c)(1),
(2), (4) Date: Jan. 10, 2006

(87) PCT Pub. No.: WO2005/089788

PCT Pub. Date: Sep. 29, 2005

(65) Prior Publication Data

US 2006/0204501 A1 Sep. 14, 2006

(30) Foreign Application Priority Data

Mar. 19, 2004 (JP) .............................. 2004-080454

(51) Int. Cl.
*A61K 39/395* (2006.01)
*C07K 16/00* (2006.01)
(52) U.S. Cl. .............. 424/155.1; 424/130.1; 424/133.1; 514/12
(58) Field of Classification Search ........................ None
See application file for complete search history.

(56) References Cited

U.S. PATENT DOCUMENTS 5,304,633 A * 4/1994 Tomita et al. .................. 514/12
5,317,084 A 5/1994 Tomita et al.
6,333,311 B1 * 12/2001 Nuijens et al. ................. 514/12

FOREIGN PATENT DOCUMENTS

| JP | 63-051337 | 3/1988 |
| JP | 5-238948 | 9/1993 |
| JP | 07-179355 | 7/1995 |
| JP | 07-309771 | 11/1995 |
| JP | 08-073499 | 3/1996 |
| JP | 08-291198 | 11/1996 |
| JP | 10-059864 | 3/1998 |
| JP | 63-186260 | 8/1998 |
| JP | 2000-229881 | 8/2000 |
| WO | WO 98/33509 | 8/1998 |
| WO | WO 00/12541 | 3/2000 |
| WO | WO 00/12542 | 3/2000 |

OTHER PUBLICATIONS

Skolnick et al. (Trends in Biotech., 18(1):34-39, 2000.*
Lazar et al Molecular and Cellular Biology Mar 1988 vol. 8 No. 3 1247-1252.*
Burgess et al, Journal of Cell Biology vol. 111 Nov. 1990 2129-2138.*
Schwartz et al, Proc Natl Acad Sci USA vol. 84:6408-6411 (1987).*
Lin et al Biochemistry USA vol. 14:1559-1563 (1975).*
Translation of JP 2000-229881.*
Trnaslation of JP 08-073499.*
Database Caplus on Stn (2004) Abstract No. 2004:407504.
Notice of Reason for Rejection dated Sep. 5, 2006 issued to a related Japanese application with English translation.
Ogura M., Saishin Igaku, vol. 58, No. 12, pp. 102-121, 2003.
*Current Immunology Illustrated*, S. Koyasu, editor, pp. 41-43, 2003.
Hatake K., *Hematology Frontier*, vol. 12, No. 11, pp. 65-71, 2002.
Smith, "Rituximab (monoclonal anti-CD20 antibody): Mechanisms of Action and Resistance," *Oncogene*, vol. 22, pp. 7359-7368, 2003.
Berglund, et al. "A Rapid Analytical Technique for Flow Cytometric Analysis of Cell Viability Using Calcofluor White M2R," *Cytometry*, vol. 8, No. 4, pp. 421-426, 1987.
*Molecular Medicine*, vol. 40, No. 10, pp. 1176-1181, 2003.
Eliassen, et al. "Enhanced Antitumour Activity of 15-Residue Bovine Lactoferricin Derivatives Containing Bulky Aromatic Amino Acids and Lipophilic N-Terminal Modifications," *Journal of Peptide Science*, vol. 9, pp. 510-517, 2003.
Eliassen, et al. "Evidence for a Direct Antitumor Mechanism of Action of Bovine Lactoferricin," *Anticancer Research*, vol. 22, pp. 2703-2710, 2002.
Iigo, et al. "INhibitory Effects of Bovine Lactoferrin on Colon Carcinoma 26 Lung Metastasis in Mice," *Clinical & Experimental Metastasis*, vol. 17, pp. 35-40, 1999.
Sakurai, et al. "Rituximab ni yoru Hotai Isonsei no Saibo Shogai Sayo (CDC) ni Oyobosu Lactoferrin Bunkaibutsu (LFH) no Tenka Koka," Rinsho Kesueki (Aug. 30, 2004), vol. 45, No. 8, p. 915, PS-2-186 with English translation.
Sakurai, et al. "Lactoferrin Bunkaibutsu (LFH) no Rituximab ni yoru Hotai Izonsei no Saibu Shogai Sayo (CDC) ni Oyobosu Tenka Koka," vol. 63rd, p. 308, P-0799 with English translation, Sep. 29-Oct. 1, 2004.
Yoo, et al. "Bovine Lactoferrin and Lactoferricin, a Peptide Derived from Bovine Lactoferrin, Inhibit Tumor Metastasis in Mice," *Japanese Journal of Cancer Research*, vol. 88, pp. 184-190, Feb. 1997.
Yoo, et al. "Apoptosis in Human Leukemic Cells Induced by Lactoferricin, a Bovine Milk Protein-Derived Peptide: Involvement of Reactive Oxygen Species," *Biochemical and Biophysical Research Communications*, vol. 237, pp. 624-628, 1997.
Yoo, et al. "Bovine Lactoferrin and Lactoferricin™ Inhibit Tumor Metastasis in Mice," *Adv. Exp. Med. Biol.*, vol. 443, pp. 285-291, 1998.
International Search Report dated Jun. 22, 2005.
Office Action in counterpart Chinese Application No. CPCH 0564 808P.

* cited by examiner

*Primary Examiner*—Sheela J Huff
(74) *Attorney, Agent, or Firm*—Knobbe, Martens, Olson & Bear, LLP (57) ABSTRACT

A lactoferrin hydrolysate mixture or lactoferrin partial peptide that can be obtained by hydrolyzing lactoferrin with a hydrolytic enzyme and has an action of enhancing cytotoxic activity of an antibody drug in an antibody therapy of cancer is used as an active ingredient of a drug for enhancing cytotoxic activity of an antibody drug in an antibody therapy of cancer.

8 Claims, 1 Drawing Sheet

Fig. 1

DRUG FOR CANCER THERAPY

RELATED APPLICATIONS

This application is the U.S. National Phase under 35 U.S.C. § 371 of International Application PCT/JP2005/004123, filed Mar. 9, 2005, which was published in a language other than English, which claims priority of JP 2004-080454, filed Mar. 19, 2004.

FIELD OF THE INVENTION

The present invention relates to a drug containing a lactoferrin hydrolysate mixture, a partial peptide of lactoferrin that can be isolated from the lactoferrin hydrolysate mixture or a partial peptide of lactoferrin that can be prepared by chemical synthesis or the like, which have an action of enhancing cytotoxic activity of an antibody drug in an antibody therapy of cancer, as an active ingredient. More precisely, the present invention relates to a drug having an action of enhancing sensibility to an antibody drug of cancer cells having resistance to the antibody drug.

RELATED ART

The mechanism for antibodies to recognize a specific antigen and eliminate foreign substances out of organisms have long been studied. Immunoglobulin preparations are well known as application of antibodies to therapeutic treatments. However, they have problems such as insufficient titer and contamination of unknown infection sources.

The invention of the monoclonal antibody preparation technique by Milstein and Kohler brought breakthroughs in various antibody techniques. Today, in the so-called post-genome era, specific genes of tumor cells and pathogenic factors and expression products thereof are being successively elucidated. The antibody techniques are greatly contributing to development of research methods targeting them and therapeutic methods by utilizing them. Moreover, further advancement of the antibody techniques in future is being strongly expected and attracting attentions.

Antibody drugs targeting malignant tumor have strikingly advanced in the field of molecular target therapy. Only two kinds of antibody drug products have been approved in Japan so far. However, currently known antibody drugs include at least those against malignant lymphoma (CD20, HLA-DR, CD5), acute myelogenous leukemia (CD33, CD66), chronic lymphocytic leukemia (CD52, CD20), acute lymphocytic leukemia (CD19, CD20, CD22), multiple myeloma (Id-idiotype, HM1.24), breast cancer (HER2/neu), epithelioma (EGF-R, VEGF), colon cancer (17-1A, CEA), ovarian cancer (CA125) and so forth (for example, refer to Non-patent document 1).

As the action mechanisms of these antibody drugs against malignant tumor, roughly three kinds of mechanisms are considered. That is, the first are mechanisms in which, when antibodies bind to a surface of malignant tumor cell, certain signals are transmitted to the tumor cell to cause cell death. The second are mechanisms in which the effector cells (neutrophil, macrophage, NK cell etc.) existing in organisms recognize antibodies binding to tumor cells by antigen-antibody reactions. And they kill the tumor cells by the cytotoxic activity thereof. The third are mechanisms in which the complement components in organisms recognize antibodies binding to tumor cells by antigen-antibody reactions. And they induce cytotoxic action by a classical pathway among activation pathways of the complement system to kill the tumor cell (for example, refer to Non-patent document 2).

Many cancer patients could have been survived by the development of antibody drugs. However, reports have shown many cases where a treatment with an antibody drug had become difficult due to recurrence of malignant tumors acquiring resistance to the antibody drugs in the process of performing the treatments. Accordingly, combination therapies with a chemotherapeutic agents have been examined. However, they have problems such as restriction of treatments for preventing adverse reactions (for example, refer to Non-patent document 3).

As a mechanism of acquisition of resistance to the an antibody drugs by tumor cells, many cases have been reported where expression of molecules called complement regulatory factors (CD46, CD55, CD59) increased on the surface of tumor cells. They inactivate the classical pathway of complements in the aforementioned third action mechanism, leading to the acquisition of the resistance (for example, refer to Non-patent document 4). It has been suggested that cytotoxic activity of the complement systems are degraded by such a mechanism, resulting in reduction of sensibility of target tumor cells to antibody drugs. Thus, development of a technique improving cytotoxic activity of the complement system against malignant tumor having resistance to an antibody drug has been desired.

Lactoferrin is a nonheme iron binding glycoprotein which exists in milk, saliva, tear, sperm, various mucus and so forth of mammals, and is a multifunctional protein having iron adsorption action, cell growth promoting action, immunoregulatory action and antimicrobial action. Bovine lactoferrin can be easily obtained in a large amount from raw skimmed milk or cheese whey routinely handled in dairy factories and can be readily utilized as a commercial product.

Lactoferricin (registered trade name of the applicant of the present invention) is a novel peptide isolated from an enzymatic hydrolysate of bovine lactoferrin by the inventors of the present invention for the first time (for example, refer to Patent document 1). Lactoferricin isolated from bovine lactoferrin has, for example, the amino acid sequence of SEQ ID NO: 2. Lactoferricin is an extremely useful substance that exhibits an antimicrobial action at a low concentration on a wide range of microorganisms such as Gram-positive and Gram-negative bacteria and yeast that cause various diseases in humans and other animals. Most of other clinically used antimicrobial agents including antibiotics are chemical substances, which are foreign to human and animals. However, lactoferricin is a natural peptide that does not contain any chemical substance or chemically synthesized amino acid derivative, and therefore it is healthy and safe for human and animals. This is because lactoferricin is naturally produced in human stomach by decomposition of lactoferrin contained in usually ingested cow's milk by gastric pepsin. Therefore, lactoferricin can be utilized as a safe and effective antimicrobial agent in a wide variety of commercial products such as eye drops, buccals, cosmetics, skin lotions, therapeutic food and products for pets, and thus has an extremely great value.

Concerning the anti-tumor effect of lactoferrin, an antitumor drug (Patent document 2), parenteral antitumor drug (Patent document 3), cancer metastasis inhibitor which is to be orally administered (Patent document 4) and so forth have been disclosed so far. These techniques all utilize effect of lactoferrin directly acting on tumor cells, and the effects are different from the antitumor effect attributable to enhancement of cytotoxic activity of an antibody drug in an antibody therapy, which draws attention in recent cancer therapy. That is, it has been unknown that a lactoferrin hydrolysate mixture or a partial peptide of lactoferrin have an effect of enhancing cytotoxic activity of an antibody drug in an antibody therapy of cancer, in particular, antibody therapy of drug-resistant cancer.

[Patent document 1] Japanese Patent No. 2818056
[Patent document 2] Japanese Patent Laid-open (Kokai) No. 63-51337
[Patent document 3] Japanese Patent Laid-open No. 7-309771
[Patent document 4] Japanese Patent Laid-open No. 10-59864
[Non-patent document 1] Ogura M., Saishin Igaku, Vol. 58, No. 12, pp. 102-121, 2003
[Non-patent document 2] Koyasu S. ed., Kinoshita T., Current Immunology Illustrated, pp. 41-43, 2003
[Non-patent document 3] Hatake K., Blood Frontier, Vol. 12, No. 11, pp. 65-71, 2002
[Non-patent document 4] Oncogene, Vol. 22, pp. 7359-7368, 2003

SUMMARY OF THE INVENTION

An object of the present invention is to provide a highly safe drug which causes no adverse reaction and has an action of enhancing cytotoxic activity of the antibody drugs in the antibody therapies of cancer, in particular, drug-resistant cancer, food or drink containing the drug and a method for enhancing cytotoxic activity of the antibody drugs.

While paying attention to techniques for more effectively enhancing cytotoxic activity of antibody drugs leading to improvement of treatment results, the inventors of the present invention considered that, if we could enhance the sensibility of target tumor cells to the antibody drugs, the cytotoxic activity of the complement system should be sufficiently exhibited even if resistance to the antibody drug is confirmed in a patient with malignant tumor, and assiduously conducted research and development. As a result, they found that a lactoferrin hydrolysate mixture and a peptide that could be isolated from the lactoferrin hydrolysate mixture acted on target tumor cells to enhance sensibility of the cells to an antibody drug in an experimental system where a cytotoxic effect is caused by antibody and complement, and thus achieved the present invention.

That is, the present invention relates to a novel drug containing a lactoferrin hydrolysate mixture or a partial peptide of lactoferrin isolated from the lactoferrin hydrolysate mixture or a partial peptide of lactoferrin that can be prepared by chemical synthesis or the like as an active ingredient based on its action of enhancing cytotoxic activity of the antibody drugs, which is essentially different from the conventionally known antitumor effect of lactoferrin, in the antibody therapy considered to be particularly effective for cancer for which almost no effective therapies or drugs have found so far and, and use thereof.

The first invention of the present invention that achieves the aforementioned object is a drug for enhancing cytotoxic activity of the antibody drugs in the antibody therapies of cancer, which comprises a lactoferrin hydrolysate that can be obtained by hydrolyzing lactoferrin with a hydrolytic enzyme and has an action of enhancing cytotoxic activity of the antibody drug in an antibody therapy of cancer as an active ingredient.

The aforementioned first invention may be characterized by the following 1) to 6) as preferred embodiments.
1) The aforementioned hydrolytic enzyme is pepsin.
2) The degradation rate of the aforementioned lactoferrin hydrolysate is 6 to 20%.
3) The aforementioned lactoferrin hydrolysate has a number average molecular weight of 500 to 5000.
4) The aforementioned cancer is any one of breast cancer, B-cell lymphoma and colon cancer.
5) The aforementioned cancer is a cancer having resistance to an antibody drug.
6) The aforementioned action of enhancing cytotoxic activity of an antibody drug is an action of increasing sensibility of target tumor cells to the antibody drug.

Another embodiment of the aforementioned first invention is use of the aforementioned lactoferrin hydrolysate for production of the aforementioned drug. Furthermore, another embodiment of the aforementioned first invention is a method for enhancing cytotoxic activity of an antibody drug in an antibody therapy of cancer using the antibody drug, wherein the aforementioned lactoferrin hydrolysate is administered to a patient.

The second invention of the present invention that achieves the aforementioned object is a drug for enhancing cytotoxic activity of an antibody drug in an antibody therapy of cancer, which comprises any one type or a mixture of two or more types of the following peptides of (a) to (d) as an Active Ingredient:
(a) a peptide having the amino acid sequence of SEQ ID NO: 2;
(b) a peptide having the amino acid sequence of the amino acid numbers 36 to 60 in the amino acid sequence of SEQ ID NO: 1, which includes substitution, deletion, addition or inversion of one or more amino acid residues, and having an action of enhancing cytotoxic activity of an antibody drug in an antibody therapy of cancer;
(c) a peptide having the amino acid sequence of SEQ ID NO: 3;
(d) a peptide having the amino acid sequence of the amino acid numbers 36 to 61 in the amino acid sequence of SEQ ID NO: 1, which includes substitution, deletion, addition or inversion of one or more amino acid residues, and having an action of enhancing cytotoxic activity of an antibody drug in an antibody therapy of cancer.

The aforementioned second invention may be characterized by the following 7) to 9) as preferred embodiments.
7) The aforementioned cancer is any one of breast cancer, B-cell lymphoma and colon cancer.
8) The aforementioned cancer is a cancer having resistance to an antibody drug.
9) The aforementioned action of enhancing cytotoxic activity of an antibody drug is an action of increasing sensibility of target tumor cells to the antibody drug.

Another embodiment of the aforementioned second invention is use of the aforementioned peptide for production of the aforementioned drug. Furthermore, another embodiment of the aforementioned second invention is a method for enhancing cytotoxic activity of an antibody drug in an antibody therapy of cancer using the aforementioned antibody drug, wherein the aforementioned lactoferrin hydrolysate is administered to a patient.

Furthermore, the present invention provides food or drink comprising the drug of the aforementioned first or second invention.

The third invention of the present invention that achieves the aforementioned object is food or drink comprising a lactoferrin hydrolysate that can be obtained by hydrolyzing lactoferrin with a hydrolytic enzyme and has an action of enhancing cytotoxic activity of an antibody drug used in an antibody therapy of cancer, which is attached with an indication that the food or drink is used for enhancing cytotoxic activity of an antibody drug used for an antibody therapy of cancer.

The fourth invention of the present invention that achieves the aforementioned object is a drug for an antibody therapy of cancer, which comprises a lactoferrin hydrolysate that can be obtained by hydrolyzing lactoferrin with a hydrolytic enzyme and an antibody drug as active ingredients.

The aforementioned fourth invention may be characterized by the following 10) to 14) as preferred embodiments.

10) The aforementioned hydrolytic enzyme is pepsin.
11) The degradation rate of the aforementioned lactoferrin hydrolysate is 6 to 20%.
12) The aforementioned lactoferrin hydrolysate has a number average molecular weight of 500 to 5000.
13) The aforementioned antibody drug is an anti-CD20 antibody, anti-HER2 monoclonal antibody or anti-17-1A (human tumor-related epithelial cell adhesion factor) antibody.
14) The aforementioned cancer is a cancer having resistance to an antibody drug.

The fifth invention of the present invention that achieves the aforementioned object is a drug for an antibody therapy of cancer, which comprises any one type or a mixture of two or more types of the following peptides of (a) to (d) and an Antibody Drug as Active Ingredients:

(a) a peptide having the amino acid sequence of SEQ ID NO: 2;
(b) a peptide having the amino acid sequence of the amino acid numbers 36 to 60 in the amino acid sequence of SEQ ID NO: 1, which includes substitution, deletion, addition or inversion of one or more amino acid residues, and having an action of enhancing cytotoxic activity of an antibody drug in an antibody therapy of cancer;
(c) a peptide having the amino acid sequence of SEQ ID NO: 3;
(d) a peptide having the amino acid sequence of the amino acid numbers 36 to 61 in the amino acid sequence of SEQ ID NO: 1, which includes substitution, deletion, addition or inversion of one or more amino acid residues, and having an action of enhancing cytotoxic activity of an antibody drug in an antibody therapy of cancer.

The aforementioned fifth invention may be characterized by the following 15) and 16) as preferred embodiments.

15) The aforementioned antibody drug is an anti-CD20 antibody, anti-HER2 monoclonal antibody or anti-17-1A (human tumor-related epithelial cell adhesion factor) antibody.
16) The aforementioned cancer is a cancer having resistance to an antibody drug.

The present invention relates to a drug for enhancing cytotoxic activity of an antibody drug in an antibody therapy of cancer, which comprises a lactoferrin hydrolysate mixture, a partial peptide of lactoferrin that can be isolated from the lactoferrin hydrolysate mixture or a partial peptide of lactoferrin that can be prepared by chemical synthesis or the like as an active ingredient, and target tumor cells can be efficiently killed or injured by enhancing cytotoxic activity of complement and antibody drug.

Furthermore, the drug of the present invention also has an effect of recovering cytotoxic activity of complement and antibody drug, in particular, against tumor cells having resistance to the antibody drug. Furthermore, the active ingredient of the drug of the present invention for therapeutic treatment of cancer having resistance can be obtained from a relatively inexpensive raw material such as cow's milk and therefore produced in a large scale.

Furthermore, the aforementioned active ingredient also exerts the same effect as that of the aforementioned drug when it is contained in food or drink, which is attached with an indication that the food or drink is for enhancing cytotoxic activity of an antibody drug in an antibody therapy of cancer.

BEST MODE FOR CARRYING OUT THE INVENTION

Hereafter, preferred embodiments of the present invention will be explained in detail. However, the present invention is not limited to the preferred embodiments described below and can be freely modified within the scope of the present invention. In the present specification, percentage is used on mass basis unless otherwise indicated.

The active ingredient of the drug for enhancing cytotoxic activity of an antibody drug in an antibody therapy of cancer or the drug for an antibody therapy of cancer of the present invention (henceforth also referred to simply as "the drug of the present invention") is a lactoferrin hydrolysate that can be obtained by hydrolyzing lactoferrin with a hydrolytic enzyme and has an action of enhancing cytotoxic activity of an antibody drug in an antibody therapy of cancer (henceforth also referred to as "lactoferrin hydrolysate mixture") or any one type or a mixture of two or more types of the following peptides of (a) to (d) (Hereinafter, also Referred to as "Partial Peptide of Lactoferrin"):

(a) a peptide having the amino acid sequence of SEQ ID NO: 2;
(b) a peptide having the amino acid sequence of the amino acid numbers 36 to 60 in the amino acid sequence of SEQ ID NO: 1, which includes substitution, deletion, addition or inversion of one or more amino acid residues, and having an action of enhancing cytotoxic activity of an antibody drug in an antibody therapy of cancer;
(c) a peptide having the amino acid sequence of SEQ ID NO: 3;
(d) a peptide having the amino acid sequence of the amino acid numbers 36 to 61 in the amino acid sequence of SEQ ID NO: 1, which includes substitution, deletion, addition or inversion of one or more amino acid residues, and having an action of enhancing cytotoxic activity of an antibody drug in an antibody therapy of cancer.

SEQ ID NO: 2 corresponds to the amino acid numbers 36 to 60 in SEQ ID NO: 1. Furthermore, SEQ ID NO: 3 corresponds to the amino acid numbers 36 to 61 in SEQ ID NO: 1.

In the present invention, the term "antibody drug used for an antibody therapy of cancer" means a drug that contains an antibody binding to a surface of a cancer cell as an active ingredient and kills or injures the cancer cell by binding of the aforementioned antibody to the cancer cell. Actions of the antibody drug include inhibition of a cancer cell growth signal, killing or injuring cancer cells by activating a cell death signal, killing or injuring cancer cells by a complement-dependent cytotoxicity or antibody-dependent cellular-cytotoxicity, and so forth.

In the present invention, the expression "enhancing cytotoxic activity" encompasses, besides an effect of enhancing cytotoxic activity of an antibody drug in an antibody therapy of cancer, that is, enhancing an action of a complement and/or an antibody drug to kill or injure target tumor cells, an action of increasing sensibility to an antibody drug of tumor cells having resistance to the antibody drug, that is, recovering cytotoxic activity of the complement and/or the antibody drug. Furthermore, the expression "having resistance to an antibody drug" means having resistance to an action of an antibody drug or complement to kill or injure tumor cells (cytotoxic activity). In other words, it means that the aforementioned action may be weak, or the tumor cells do not incur the action. Furthermore, resistance to an antibody drug is not limited to resistance caused by a complement regulatory factor, and include resistance to an antibody drug caused by other factors.

A lactoferrin hydrolysate mixture and a partial peptide of lactoferrin that can be isolated from the lactoferrin hydrolysate mixture (lactoferrin partial peptide), the active ingredient of the drug of the present invention, can be prepared by using lactoferrin as a starting material. As lactoferrin, there can be used commercially available lactoferrins and lactoferrins obtained from colostrum, transitional milk, nature milk or late lactation milk of mammals (for example, human, bovine and so forth) or processed products of these milks such as skimmed milk and whey as a raw material by isolating from the aforementioned raw materials with a conventional technique such as ion exchange chromatography. In particular, commercially available lactoferrin produced in an industrial scale (for example, one produced by Morinaga Milk Industry Co., Ltd.) can be preferably used. Furthermore, lactoferrins produced with microorganisms, animal cells, transgenic animals and so forth by using genetic engineering techniques can also be used.

Furthermore, a peptide having an amino acid sequence similar to that of a peptide that can be isolated from the lactoferrin hydrolysate mixture (lactoferrin partial peptide) can also be directly prepared by chemical synthesis, genetic engineering techniques or the like.

Examples of the method for preparing a lactoferrin hydrolysate mixture, the active ingredient of the drug of the present invention, by using such lactoferrin include a method of hydrolyzing lactoferrin with a hydrolytic enzyme or the like in a conventional manner. As for specific method, the enzyme used for the hydrolysis of lactoferrin may be any hydrolytic enzyme so long as it is an enzyme that decomposes lactoferrin to produce peptides having an action of enhancing cytotoxic activity of an antibody drug in an antibody therapy of cancer or a mixture thereof.

Examples of the hydrolytic enzyme include pepsin, pancreatine, trypsin, chymotrypsin, proteases derived from *Aspergillus oryzae* or *Streptomyces griseus* and so forth. One or more types of hydrolytic enzymes may be used. When two or more types of enzymes are used, the enzymatic reactions may be performed simultaneously or separately. In the present invention, pepsin is particularly preferably used. Furthermore, it is also possible to use an endo-type protease in combination with an exo-type hydrolytic enzyme. The hydrolysis reaction time is preferably determined so that a preferred degradation rate can be attained while monitoring the degradation rate of the enzymatic reaction. To obtain a lactoferrin hydrolysate mixture, the active ingredient of the drug of the present invention, the degradation rate is preferably 6 to 20%, particularly preferably 8 to 12%.

The degradation rate of a protein can be calculated by, for example, measuring total nitrogen content of a sample by the Kjeldahl method (Ed. by The Japanese Society for Food Science and Technology, "Food Analysis Methods," p. 102, Korin, 1984), measuring formol nitrogen content of the sample by the formol titration method (Ed. by Mitsuda et al., "Laboratory Manual of Food Engineering," First Volume, p. 547, Yokendo Co., Ltd., 1970) and using these measured values in the following equation.

$$\text{Degradation rate (\%)} = \left(\frac{\text{Formol nitrogen content}}{\text{Total nitrogen content}}\right) \times 100$$

When a preferred degradation rate is attained, the enzymatic reaction may be terminated. The enzymatic reaction can be terminated by inactivation of the enzyme in the hydrolysis solution, which can be carried out by a heat inactivation treatment in a conventional manner. The heating temperature and retention time of the heat inactivation treatment can be suitably selected as conditions enabling sufficient inactivation taking into account thermal stability of the used enzyme, and, for example, the inactivation can be performed in the temperature range of 80 to 130° C. for a retention time of 30 minutes to 2 seconds. The obtained reaction mixture is preferably adjusted to be within the pH range of 5.5 to 7 with an acid such as citric acid. When the lactoferrin hydrolysate mixture contains insoluble substances, it can be removed by either centrifugation or filtration.

In the present invention, the number average molecular weight of the lactoferrin hydrolysate mixture is preferably 500 to 5000, particularly preferably 1000 to 4000.

As described in, for example, the literature (The Society of Polymer Science, Japan, ed., "Fundamentals of Polymer Science", pp. 116-119, Tokyo Kagaku Dozin Co., Ltd., 1978), the number average molecular weight represents an average molecular weight of a macromolecular compound on the basis of different indexes as described below.

That is, a macromolecular compound such as protein hydrolysate is a heterogeneous substance, and the molecular weights of individual molecules have a distribution. Therefore, the molecular weight of a protein hydrolysate needs to be represented by an average molecular weight for physicochemically addressing it. The number average molecular weight (henceforth also abbreviated as Mn) is an average with regard to the number of molecules. When the molecular weight of a peptide chain i is Mi, and the number of molecules thereof is Ni, Mn is defined by the following equation:

$$Mn = \sum_{i=1}^{\infty} MiNi \Big/ \sum_{i=1}^{\infty} Ni \qquad \text{Equation 1}$$

The lactoferrin hydrolysate mixture obtained as described above can be utilized as an active ingredient of the drug of the present invention as it is, or can be lyophilized or spray-dried in a conventional manner and stored as powder. Furthermore, it can also be utilized for production of a lactoferrin partial peptide, another active ingredient of the drug of the present invention. Furthermore, the lactoferrin hydrolysate mixture may be obtained by adding a lactoferrin partial peptide to a hydrolysis product of lactoferrin obtained as above.

Specific examples of the aforementioned lactoferrin partial peptide include a peptide having the amino acid sequence of the amino acid numbers 36 to 60 in the amino acid sequence of SEQ ID NO: 1 shown in Sequence Listing and a peptide having the amino acid sequence of the amino acid numbers 36 to 61 in the amino acid sequence of SEQ ID NO: 1 shown in Sequence Listing (SEQ ID NO: 2). Hereinafter, the peptide having the amino acid sequence of the amino acid numbers 36 to 60 (SEQ ID NO: 3) is also referred to as lactoferrin $F_{36}$-$F_{60}$, and the aforementioned peptide having the amino acid sequence of the amino acid numbers 36 to 61 is also referred to as lactoferrin $F_{36}$-$A_{61}$.

When peptides comprising both the lactoferrin $F_{36}$-$F_{60}$ and lactoferrin $F_{36}$-$A_{61}$ are used as the active ingredients, the mixing ratio of the lactoferrin $F_{36}$-$F_{60}$ and lactoferrin $F_{36}$-$A_{61}$ is preferably 1:20 to 20:1 (lactoferrin $F_{36}$-$F_{60}$:lactoferrin $F_{36}$-$A_{61}$), particularly preferably 1:10 to 2:3 (lactoferrin $F_{36}$-$F_{60}$: lactoferrin $F_{36}$-$A_{61}$).

The lactoferrin partial peptide, specifically the lactoferrin $F_{36}$-$F_{60}$ and/or lactoferrin $F_{36}$-$A_{61}$, can be prepared, for example, according to the method for producing lactoferricin described in Japanese Patent Laid-open (Kokai) No. 5-238948 by using a lactoferrin hydrolysate mixture prepared as described above as a starting material. Further, the lactoferrin $F_{36}$-$F_{60}$ and/or lactoferrin $F_{36}$-$A_{61}$ may be any of a peptide prepared by a method of producing a synthetic peptide by chemical synthesis, a peptide produced by a method of producing it by synthesis of a recombinant peptide using a genetic engineering technique utilizing a gene recombination technique etc. and so forth, so long as it is a peptide having the amino acid sequence of the amino acid numbers 36 to 60 and/or the amino acid numbers 36 to 61 in the amino acid sequence of SEQ ID NO: 1. For example, as for the method of using a genetic engineering technique, the lactoferrin partial peptide can be obtained by preparing suitable primers on the basis of a nucleotide sequence encoding an amino acid sequence including a region of interest, amplifying the nucleotide sequence by PCR using the aforementioned primers and cDNA including the target nucleotide sequence as a template and expressing the obtained nucleotide sequence using a suitable expression system.

Furthermore, usual genes may contain a mutation such as substitution, deletion, insertion, addition or inversion of one or more nucleotides at one or more positions due to difference in species, genus, individuals and so forth, and amino acid residues of a protein encoded by a gene having such a mutation may also have a mutation. The lactoferrin $F_{36}$-$F_{60}$ and lactoferrin $F_{36}$-$A_{61}$ that can be used for the present invention including such a mutation also fall within the scope of the present invention so long as the action of enhancing cytotoxic activity of an antibody drug in an antibody therapy of cancer having resistance is not degraded. The number of substituted, deleted, inserted, added or inverted amino acid residues that may be included in the lactoferrin $F_{36}$-$F_{60}$ or lactoferrin $F_{36}$-$A_{61}$ is preferably 1 to 12, more preferably 1 to 8, most preferably 1 to 5. Furthermore, the substitution of amino acid residues is preferably substitution of amino acids having similar property, i.e., so-called conservative substitution. If such a modified lactoferrin $F_{36}$-$F_{60}$ or lactoferrin $F_{36}$-$A_{61}$ is longer than the lactoferrin $F_{36}$-$F_{60}$ or lactoferrin $F_{36}$-$A_{61}$, the added amino acid(s) is(are) preferably amino acid(s) corresponding to a sequence on the N-terminus side from the 36th position or on the C-terminus side from the 60th or 61st position of the lactoferrin. However, so long as the aforementioned modified lactoferrin $F_{36}$-$F_{60}$ or lactoferrin $F_{36}$-$A_{6}$, has a desired action, the added amino acid(s) may be an arbitrary amino acid(s).

The lactoferrin hydrolysate mixture or lactoferrin partial peptide that can be used for the present invention has an action of enhancing cytotoxic activity of an antibody drug in an antibody therapy of cancer, and the action can be measured according to a method using propidium iodide (PI, Dojindo, catalog No. P378) [Cytometry, Vol. 8, No. 4, pp. 421-426, 1987] or a method using calcein-AM (Dojindo, catalog No. 341-07901) [Apoptosis, Vol. 3, No. 3, pp. 195-202, 1998]. In the examples described later, the measurement method will be explained in detail.

As the drug of the present invention, a lactoferrin hydrolysate mixture or a lactoferrin partial peptide can be orally or parenterally administered to a mammal including human in combination with a pharmaceutically acceptable carrier for pharmaceutical preparations. As the drug for an antibody therapy of cancer of the present invention, an antibody drug is further used in combination with the aforementioned components. The dosage form of the drug of the present invention is not particularly limited, and can be suitably selected depending on the purpose of therapeutic treatment. Specific examples thereof include tablets, pills, powders, solutions, suspensions, emulsions, granules, capsules, syrups, suppositories, injections, ointments, patches, eye drops, nasal drops and so forth. In the production of the pharmaceutical preparation, additives commonly used for usual agents as pharmaceutical carriers such as excipients, binders, disintegrating agents, lubricants, stabilizers, flavoring agents, diluents, surfactants and solvents for injection can be used.

The amount of the lactoferrin hydrolysate mixture or lactoferrin partial peptide contained in the drug of the present invention is not particularly limited and can be suitably selected. However, for example, the concentration of lactoferrin hydrolysate mixture contained in the pharmaceutical preparation may be 10 μg/ml to 50 mg/ml, preferably 50 μg/ml to 10 mg/ml, and the concentration of lactoferrin partial peptide in the preparation may be 0.5 to 200 μg/ml, preferably 1 to 100 μg/ml.

The administration time of the drug of the present invention is not particularly limited, and it can be administered before or after administration of an antibody drug or simultaneously with an antibody drug. The administration time can be suitably selected according to the method of therapeutic treatment for the objective cancer type. The administration method is suitably selected also depending on the dosage form, age, sex and other conditions of patients, severity of symptoms of patients and so forth.

The dose of the active ingredient contained in the pharmaceutical preparation of the present invention is suitably selected depending on the administration method, age, sex and severity of disease of patients, other conditions and so forth. The dose of the lactoferrin hydrolysate mixture or lactoferrin partial peptide as the active ingredient is preferably in the range of 0.001 to 60 mg/kg/day, preferably 0.01 to 20 mg/kg/day, as a guideline, and the dose can be given once a day or at two or more times a day as divided portions.

The drug of the present invention is useful as a curative drug, a curative effect enhancing drug or a auxiliary curative drug in a therapeutic treatment using an antibody drug for a cancer, for example, any one of breast cancer, B cell lymphoma and colon cancer. Moreover, among the drugs of the present invention, the drug comprising an antibody drug together with a lactoferrin hydrolysate mixture or a lactoferrin partial peptide can be used as a drug for antibody therapy of cancer. In addition, even when the drug for antibody therapy of cancer of the present invention is used, an antibody drug or the drug for enhancing cytotoxic activity of an antibody drug of the present invention can also be further administered. The drugs of the present invention exhibit extremely marked efficacy against, in particular, cancer having resistance to an antibody drug among the aforementioned cancers. Examples of the antibody drug usable for the present invention include an anti-CD20 antibody (rituximab), anti-HER2 monoclonal antibody (trastuzumab), anti-17-1A (adhesion molecules of human epithelioma) antibody (edrecolomab) and so forth. In addition, antibody drugs usable in antibody therapy for cancer therapy can also be used. Moreover, not only the presently known antibody drugs, but also antibody drugs to be developed in future can also be used.

The drugs of the present invention are preferably used in antibody therapy together with an antibody drug (it is not limited whether they are simultaneously administered or separately administered), and it is also possible to use them together with a known prophylactic or therapeutic drug (including an enhancing drug and auxiliary drug) for any of the aforementioned cancers in combination. The combined use can enhance the prophylactic and therapeutic effect for the aforementioned cancerous diseases, and can also reduce dose of the aforementioned prophylactic or therapeutic drug used in combination. Furthermore, the prophylactic or therapeutic drug for the aforementioned cancers to be used in combination may be contained in the compositions of the drugs of the present invention as an active ingredient, or it may not be contained in the compositions of the drugs of the present invention, but combined as a separate drug to constitute a commercial product and combined upon use.

The drug of the present invention or the lactoferrin hydrolysate mixture or lactoferrin partial peptide as active ingredient of the drug may be contained in food or drink. Form and property of the food or drink are not particularly limited so long as the effect of the active ingredient is not degraded, and the food or drink can be orally ingested, and they can be produced in a conventional manner by using raw materials usually used for food or drink except that the aforementioned active ingredient is added.

The use of food or drink of the present invention may be any of various uses for enhancing cytotoxic activity of an antibody drug used for antibody therapy of cancer. Examples include, for example, use as food or drink useful for reduction or elimination of a risk factor of cancer, in particular, cancer having resistance to an antibody drug.

The food or drink of the present invention is also useful for prevention of a disease caused by a cancer having resistance to an antibody drug and so forth. Furthermore, the food or drink of the present invention can prevent various diseases, complications thereof and so forth resulting from a cancer having resistance to an antibody drug and reduce risks of these diseases, complications thereof and so forth.

The food or drink of the present invention is preferably sold as food or drink attached with an indication "For use for enhancing cytotoxic activity of an antibody drug used for antibody therapy of cancer", for example, "food or drink containing a drug for enhancing cytotoxic activity of an antibody drug used for antibody therapy of cancer indicated as 'For enhancing cytotoxic activity of an antibody drug used for antibody therapy of cancer'" or "food or drink containing a lactoferrin hydrolysate mixture or a lactoferrin partial peptide indicated as 'For enhancing cytotoxic activity of an antibody drug used for antibody therapy of cancer'", or "food or drink containing a compound having an effect of enhancing cytotoxic activity of an antibody drug used for antibody therapy of cancer", or "food or drink containing a hydrolysate of lactoferrin indicated as 'For enhancing cytotoxic activity of an antibody drug used for antibody therapy of cancer'", "food or drink containing a lactoferrin partial peptide indicated as 'For enhancing cytotoxic activity of an antibody drug used for antibody therapy of cancer'", "food or drink containing a hydrolysate of lactoferrin indicated as 'For enhancing cytotoxic activity of an antibody drug used for antibody therapy of cancer'", "food or drink containing a lactoferrin partial peptide indicated as 'For enhancing cytotoxic activity of an antibody drug used for antibody therapy of cancer'", or the like. In addition, because the compounds, compositions and so forth of the present invention have an action of enhancing cytotoxic activity of an antibody drug used for antibody therapy of cancer, the food or drink of the present invention can be indicated as "For enhancing cytotoxic activity of an antibody drug used for antibody therapy of cancer".

The wording for such an indication as described above is not necessarily be limited to the expression "For enhancing cytotoxic activity of an antibody drug used for antibody therapy of cancer", and any wording expressing an auxiliary effect or enhancing effect for cytotoxic activity of an antibody drug used for antibody therapy of cancer of course falls within the scope of the present invention. As such a wording, an indication based on various uses allowing consumers to recognize enhancing effect for cytotoxic activity of an antibody drug used for antibody therapy of cancer or an auxiliary or enhancing effect for an antibody drug used for antibody therapy of cancer is also possible. Examples include, for example, an indication "Useful for reduction and elimination of risk factors of cancer having resistance to an antibody drug etc." In addition, in the aforementioned indication, the wording of "used for antibody therapy of cancer" may be omitted.

The aforementioned term "indication" include all actions for informing consumers of the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods, or providing information including those as contents with indicating the aforementioned use by an electromagnetic method (Internet etc.) and so forth.

The indication is preferably an indication approved by the administration etc. (for example, an indication in a form based on an approval, which is qualified on the basis of any of various legal systems provided by the administration), and it is particularly preferably an indication on packages, containers, catalogs, pamphlets and advertisement materials at the sales spots such as POPs, others documents and so forth.

Examples of the indication further include, for example, indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

EXAMPLES

Hereafter, the present invention will be further specifically explained by referring to the following examples. However, the present invention is not limited to the following examples.

Preparation Example 1

Preparation of Lactoferrin Hydrolysate Mixture

Bovine lactoferrin isolated from skim milk (Morinaga Milk Industry Co., Ltd., purity: about 90%) in an amount of 2.0 kg was dissolved in distilled water at a concentration of 5 mass %, and the solution was adjusted to pH 3.0 by addition of 1 N hydrochloric acid. Crystalline pepsin (Difco) was added at a ratio of 3 mass % of the substrate, and hydrolysis was allowed at 37° C. for 4 hours. Then, the reaction mixture was heated at 80° C. for 15 minutes to inactivate the pepsin, and 1 N sodium hydroxide was added to adjust the reaction mixture to pH 7.0. The insoluble substances was removed by filtration, and the filtrate was spray-dried to prepare about 1.9 kg of powdered lactoferrin hydrolysate. The decomposition rate of the produced lactoferrin hydrolysate mixture was 10%.

Preparation Example 2

Preparation of Lactoferrin Hydrolyzed Peptide

A starting material prepared in the same manner as in Preparation Example 1 (lactoferrin hydrolysate mixture) in an amount of 600 g was dissolved in distilled water at a concentration of 5 mass %. About 3000 ml of a hydrophobic carrier (Butyl TOYOPERL 650 M, trade name, TOSOH CORP.) was equilibrated by sufficient washing with water. The solution of the starting material was mixed with the hydrophobic carrier in a tank provided with a stirrer, and then the solution was separated. The hydrophobic carrier was filled in a column (10 cm in length and 20 cm in diameter), and the aforementioned separated solution was loaded on the column. Then, the column was sufficiently washed by using water at a flow rate of 400 ml/minute until the absorbance of the washing solution at 280 nm became 0.06 or less.

Subsequently, 10 mmol hydrochloric acid was loaded on the column to elute lactoferrin hydrolyzed peptides, the eluate was mixed with an equal volume of McIlvaine buffer (mixture of 177 parts by volume of 0.1 M acetic acid+823 parts by volume of 0.2 M sodium primary phosphate, pH 7.0) and the peptides were adsorbed on the hydrophobic carrier. The hydrophobic carrier was filled in a column and washed with 6000 ml of the same buffer, and the lactoferrin hydrolyzed peptides were eluted with 9000 ml of McIlvaine buffer (mixture of 485 parts by volume of 0.1 M acetic acid+515 parts by volume of 0.2 M sodium primary phosphate, pH 5.0). 10 mM hydrochloric acid and water was loaded on the column to regenerate the hydrophobic carrier, and pH of the eluate was adjusted to 7.0 with 1 N sodium hydroxide solution. The aforementioned eluate containing the lactoferrin hydrolyzed peptides was passed through this column, and the column was washed with 30 l of water to remove salts of the buffer. Then, 10 mM hydrochloric acid was loaded on the column to elute the lactoferrin hydrolyzed peptides, which were lyophilized to obtain about 10.5 g of powdered lactoferrin hydrolyzed peptides. Purity of the obtained lactoferrin hydrolyzed peptides was measured by HPLC, and as a result, it was found to be 99%. Furthermore, the amino acid sequences of the lactoferrin hydrolyzed peptides were determined, and as a result, it was confirmed that the produced lactoferrin hydrolyzed peptides contained both the peptides of lactoferrin $F_{36}$-$F_{60}$ and lactoferrin $F_{36}$-$A_{61}$. The existence ratio of these peptides (lactoferrin $F_{36}$-$F_{60}$:lactoferrin $F_{36}$-$A_{61}$) was 1:6.

Hereafter, the present invention will be explained in detail with reference to the following test examples.

Test Example 1

This test was performed in order to examine the effect of addition of a lactoferrin hydrolysate mixture on cytotoxic action of complement and antibody drug.

(1) Test Samples

Test Sample 1 was prepared with the lactoferrin hydrolysate mixture prepared in Preparation Example 1, of which concentration was adjusted to 1000 μg/ml in RPMI 1640 medium (Sigma, catalog number: R8758) containing 7.5% fetal bovine serum (Gibco, catalog number: 10099-141) and 1% penicillin-streptomycin (Gibco, catalog number: 15070-063) [henceforth this solution is referred to as "dilution solution"]. Furthermore, Control Sample 1 was prepared by diluting lactoferrin to a concentration of 1000 μg/ml with the dilution solution.

As target cells for measurement of cytotoxic action of complement and antibody drug, human Burkitt lymphoma Raji cells (ATCC CCL-86, obtained from American Type Culture Collection (10801 University Boulevard, Manassas, Va. 20110-2209, USA)) were used, and the cells were suspended at a density of $2 \times 10^6$ cells/ml by using the dilution solution to prepare a Raji cell suspension. As an antibody drug solution, rituximab (Zenyaku Kogyo, sold by Nippon Roche) that recognizes the CD20 antigen was used, and it was prepared at a concentration of 200 μg/ml using the dilution solution. As a complement solution, Human serum AB (Cosmobio, catalog number: 832000027) was used. These antibody drug solution and complement solution were also used for Test Examples 2 to 5 described below.

Viability determination of the cells was performed by the method using propidium iodide (PI, Dojindo, catalog number: P378) [Cytometry, Vol. 8, No. 4, pp. 421-426, 1987] or the method using Calcein-AM (Dojindo, catalog number: 341-07901) [Apoptosis, Vol. 3, No. 3, pp. 195-202, 1998].

(2) Test Method

The Raji cell suspension was added to each well of a 24-well culture plate (NUNC, catalog number: 143982) in a volume of 100 μl each ($2 \times 10^5$ cells each). The 24 wells were divided into four groups, to wells (6 wells) of one group among them, 50 μl/well of the antibody drug solution and 250 μl/well of dilution solution were added as "Addition of antibody drug". Further, to wells (6 wells) of another group, 100 μl of the complement solution and 200 μl of the dilution solution were added as "Addition of complement". Furthermore, to wells (6 wells) of another group, 50 μl of the antibody drug solution, 100 μl of the complement solution and 150 μl of the dilution solution were added as "Addition of antibody drug+complement". To wells (6 wells) of the remaining one group, 300 μl of the dilution solution was added as "No addition".

For the aforementioned four groups, 100 μl/well of Test Sample 1 (4 groups×2 wells), Control Sample 1 (4 groups×2 wells) or the dilution solution (4 groups×2 wells) mentioned above was added as "Test Sample Group 1", "Control Sample Group 1" and "Negative Sample Group 1", respectively.

By using the 24-well plate prepared as described above, the cells were cultured under the conditions of 37° C. and 5% carbon dioxide ($CO_2$) for 1 hour using an incubator (Napco, catalog number: 5300). Then, the cells of each sample group were collected, and the rate of dead cells in each was examined by the aforementioned method using PI. Cytotoxic activity was calculated based on a case where all the target cells were killed, which was taken as 100%.

(3) Test Results

The results of this test are as shown in Table 1. As clearly seen from the results shown in Table 1, with "Addition of antibody drug+complement", cytotoxic activity was confirmed in each sample group ("Test Sample Group 1": 45.7%, "Control Sample Group 1": 24.3%, "Negative Sample Group 1": 30.7%), and it was found that, in particular, the lactoferrin hydrolysate mixture (Test Sample Group 1) markedly enhanced the cytotoxic activity (increase of about 50% compared with Negative Sample Group 1). On the other hand, the cytotoxic activity did not increase in Control Sample Group 1 compared with the negative sample group, and therefore it was found that the enhancement of cytotoxic activity was an activity specific to the lactoferrin hydrolysate mixture.

TABLE 1

| | Cytotoxic activity (%) | | |
|---|---|---|---|
| | Test Sample Group 1 | Control Sample Group 1 | Negative Sample Group 1 |
| Addition of antibody drug + complement | 45.7 | 24.3 | 30.7 |
| Addition of antibody drug | 0.9 | 1.0 | 1.0 |
| Addition of complement | 1.5 | 1.2 | 1.1 |
| No addition | 1.2 | 1.0 | 1.3 |

Test Example 2

This test was performed in order to examine change in sensibility of target tumor cells cultured with addition of the lactoferrin hydrolysate mixture during the culture for cytotoxic activity of complement and antibody drug.

(1) Test Sample

The lactoferrin hydrolysate mixture prepared in Preparation Example 1 was diluted to a concentration of 1000 µg/ml with the dilution solution used in Test Example 1 to prepare Test Sample 2.

(2) Test Method

The human Burkitt lymphoma Raji cells were suspended in 6.3 ml of the dilution solution with a cell number of $2\times10^5$ cells/culture flask (BD, catalog number: 35-3014). As for the above suspension, a group to which 0.7 ml of Test Samples 2 mentioned above was added (Test Sample Group 2) and a group to which 0.7 ml of the dilution solution was added (Negative Sample Group 2) were prepared, respectively, and the cells were cultured for three days under the conditions of 37° C. and 5% carbon dioxide ($CO_2$) using an incubator.

The cells of both the sample groups were newly added with 10 ml each of the dilution solution and centrifuged (1100 rpm×6 minutes) by using a centrifuge (KUBOTA, catalog number: 5910) to remove the supernatant. This procedure was repeated 3 times, and then the sensibility of the cells to the cytotoxic activity was examined by using the same systems as "Addition of antibody drug+complement" and "No addition" used in Test Example 1.

(3) Test Results

The result of this test are as shown in Table 2. As clearly seen from the results shown in Table 2, the sensibility to the cytotoxic activity provided by "complement+antibody drug" was clearly increased in the group of the target tumor cells cultured for 3 days with addition of the lactoferrin hydrolysate mixture (Test Sample Group 2) compared with Negative Sample Group 2, and thus it was found that the enhancing action clarified in Test Example 1 acted on the target tumor cells.

TABLE 2

| | Cytotoxic activity (%) | |
|---|---|---|
| | Test Sample Group 2 | Negative Sample Group 2 |
| Addition of antibody drug + complement | 53.9 | 34.8 |
| No addition | 1.9 | 1.5 |

Test Example 3

This test was performed in order to examine the effect of addition of a lactoferrin hydrolyzed peptide on the cytotoxicity of complement and antibody drug.

(1) Test Samples

The lactoferrin hydrolysate mixture prepared in Preparation Example 1 was diluted to a concentration of 1000 µg/ml with the dilution solution used in Test Example 1 to prepare Test Sample 3. Furthermore, the lactoferrin hydrolyzed peptide prepared by Preparation Example 2 was diluted to a concentration of 1000 µg/ml with the same dilution solution to prepare Test Sample 4.

(2) Test Method

The human Burkitt lymphoma Raji cells were suspended in the dilution solution at a density of $2\times10^5$ cells/ml to prepare a cell suspension, and this cell suspension was added to each of 18 wells of a 96-well culture plate (NUNC, catalog number: 167008) in a volume of 50 µl each ($1\times10^4$ cells each). The 18 wells were divided into two groups, to wells (9 wells) of one group, 10 µl/well of the antibody drug solution, 20 µl/well of the complement solution and 10 µl/well of the dilution solution were added as "Addition of antibody drug+complement". To wells (9 wells) of the remaining group, 40 µl of the dilution solution was added as "No addition". For each of the aforementioned 2 groups, 10 µl/well of Test Sample 3 (2 groups×3 wells), Test Sample 4 (2 groups×3 wells) or the dilution solution (2 groups×3 wells) mentioned above was added as "Test Sample Group 3", "Control Sample Group 4" and "Negative Sample Group 2", respectively.

By using the 96-well plate prepared as described above, the cells were cultured under the conditions of 37° C. and 5% carbon dioxide ($CO_2$) for 1 hour using an incubator. Then, the cells of each sample group were collected, and the rate of dead cells in each was examined by the aforementioned method using PI. Cytotoxic activity was calculated based on a case where all the target cells were killed, which was taken as 100%.

(3) Test Results

The results of this test are as shown in Table 3. As clearly seen from the results shown in Table 3, it was found that the lactoferrin hydrolyzed peptide (Test Sample Group 4) also markedly enhanced the cytotoxic activity exerted by complement and antibody (increase of about 67% compared with Negative Sample Group 2).

TABLE 3

| | Cytotoxic activity (%) | | |
| --- | --- | --- | --- |
| | Test Sample Group 3 | Test Sample Group 4 | Negative Sample Group 2 |
| Addition of antibody drug + complement | 77.4 | 86.5 | 51.9 |
| No addition | −0.1 | 3.1 | −0.5 |

Test Example 4

In this test, cytotoxic activity enhancing action (recovery of sensibility) of the lactoferrin hydrolysate mixture was examined by using target tumor cells showing different susceptibilities for cytotoxic activity of complement and antibody.

(1) Test Sample

The lactoferrin hydrolysate mixture prepared in Preparation Example 1 was diluted to a concentration of 1000 μg/ml with the dilution solution used in Test Example 1 to prepare Test Sample 5.

(2) Test Method

Lymphoma-derived Daudi cells (ATCC CCL-213, obtained from American Type Culture Collection), Raji cells (ATCC CCL-86, obtained from American Type Culture Collection), SKW6.4 cells (ATCC TIB-215, obtained from American Type Culture Collection) and lymphoma-derived ARH-77 cells (ATCC CRL-1621, obtained from American Type Culture Collection) having resistance to an antibody drug were each suspended in the dilution solution at a cell number of $2 \times 10^6$ cells/ml to prepare cell suspensions, and each cell suspension was added to a 24-well culture plate (NUNC, catalog number: 143982) in a volume of 100 μl/well ($2 \times 10^5$ each).

Examination of the cytotoxic activity was performed in the same manner as that used for the "Addition of antibody drug+ complement" system of Test Example 1. That is, to each of wells to which each cell suspension was added, 50 μl of the antibody drug solution, 100 μl of the complement solution and 150 μl of the dilution solution were added, and 100 μl of Test Sample 5 mentioned above or the dilution solution was further added as "Test Sample Group 5" and "Negative Sample Group 3", respectively.

By using the 24-well plate prepared as described above, the cells were cultured under the conditions of 37° C. and 5% carbon dioxide ($CO_2$) for 1 hour using an incubator (Napco, catalog number: 5300). Then, the cells of each sample group were collected, and the rate of dead cells in each was examined by the aforementioned method using PI. Cytotoxic activity was calculated based on a case where all the target cells were killed, which was taken as 100%.

(3) Test Results

The results of this test are as shown in Table 4. As clearly seen from the results shown in Table 4, decrease of the sensibility to the cytotoxic activity of complement and antibody by the lactoferrin hydrolysate mixture was not confirmed for the Daudi cells, which show a high sensibility to the cytotoxic activity. For the Raji and SKW6.4 cells, the effect of enhancing the cytotoxic activity of complement and antibody was confirmed.

Furthermore, for the ARH-77 cells, which are lymphoma-derived cells showing resistance to the cytotoxic activity of complement and antibody (having resistance to an antibody drug), the effect of the lactoferrin hydrolysate mixture to eliminate the resistance to the cytotoxic activity was confirmed. It was considered that this was because the lactoferrin hydrolysate mixture had an effect of enhancing the sensibility to the cytotoxic activity for tumor cells having resistance to an antibody drug and recovered the cytotoxic activity of complement and antibody drug.

TABLE 4

| | Cytotoxic activity (%) | |
| --- | --- | --- |
| | Test Sample Group 5 | Negative Sample Group 3 |
| Daudi | 97.1 | 96.4 |
| Raji | 49.0 | 27.2 |
| SKW6.4 | 38.9 | 19.8 |
| ARH-77 | 15.5 | 0.0 |

Test Example 5

In this test, the lactoferrin hydrolysate mixture, lactoferrin partial peptide and undecomposed lactoferrin etc. as control were used as samples to examine effect thereof on the cytotoxic activity of complement and antibody drug for target human Burkitt lymphoma Raji cells.

(1) Test Samples

The lactoferrin hydrolysate mixture prepared in Preparation Example 1 was used as Sample A, and the lactoferrin hydrolyzed peptide (lactoferrin partial peptide) prepared in Preparation Example 2 was used as Sample B. Moreover, as control samples, commercially available bovine lactoferrin (Morinaga Milk Industry Co., Ltd.) was used as Control A, and protamine sulfate was used as Control B.

(2) Test Method

Raji cells in the logarithmic growth phase were used as target cells. Raji cells collected by centrifugation of a cell suspension were suspended in fresh culture broth (RPMI 1640, 10% FCS), counted and then added to a 24-well plate in an amount of $1.0 \times 10^5$ cells/well. To each well, rituximab (10 mg/ml) and 1.0 mg/ml as a final concentration of Sample A, Sample B, Control A or Control B (or Medium [culture broth] instead of the sample) were added, and then human normal serum (AB type) was added at a final concentration of 10%. Then, the cells were cultured in a $CO_2$ incubator for 1 hour, and PI (propidium iodide, 1 mg/ml) was added during the last 15 minutes of the culture. After completion of the culture, all the Raji cells were collected by centrifugation to remove the supernatant, and the cell were resuspended in 0.5 ml of PBS (phosphate buffer). The Raji cells that died during the culture were counted by analyzing the suspension with a flow cytometer (FACScan) utilizing the fact that dead cells are positive in the nuclear staining with PI.

In this test, the cytotoxic activity was calculated in accordance with the following equation.

$$\text{Cytotoxic activity}(\%) = \frac{(\text{Number of } PI \text{ positive cells})}{(\text{Total cell number})} \times 100$$

(3) Test Results

Figure 1:
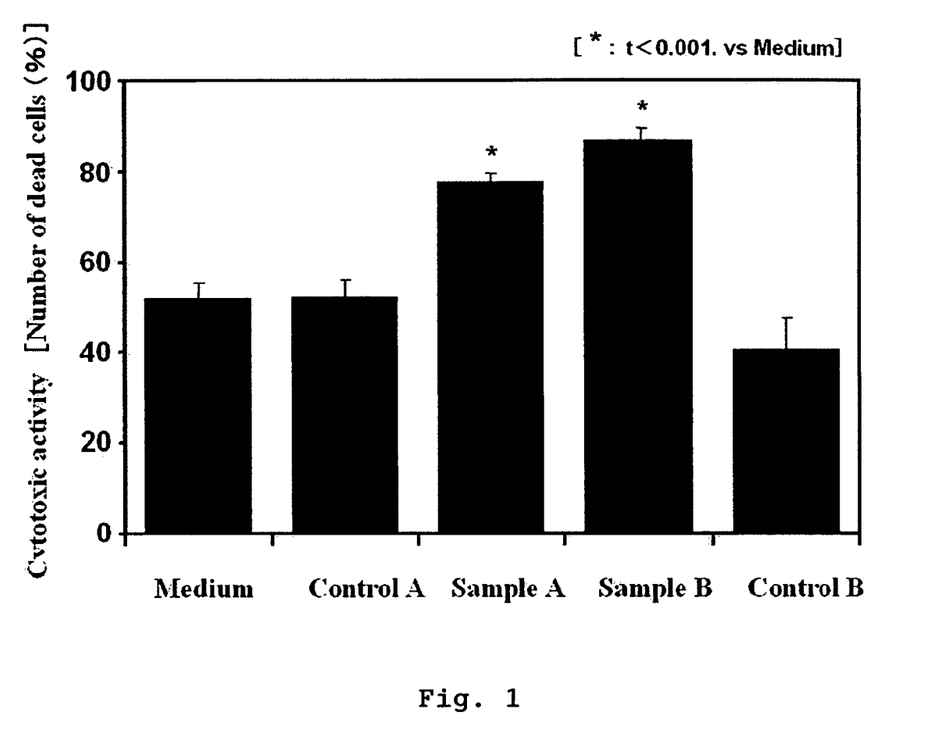
FIG. 1 shows effect of a lactoferrin hydrolysate mixture and a partial peptide of lactoferrin of the present invention on cytotoxic activity of rituximab against Raji cells. The symbol "*" denotes t<0.001 relative to Medium (culture broth).

The results of this test are as shown in FIG. 1. As clearly seen from the results shown in FIG. 1, when Control A was used as a sample, the cytotoxic activity [number of dead cells (%)] was comparable to that observed with Medium (culture broth). In contrast, when Sample A was used, the cytotoxic activity increased, and furthermore, when Sample B separated from the lactoferrin hydrolysate mixture as Sample A was used, increase of the cytotoxic activity was observed compared with that observed with Sample A. However, with addition of Control B, such increase of the activity was not observed.

That is, it was confirmed that Sample B, which was a component contained in Sample A, also had an action of enhancing CDC (complement-dependent cytotoxicity). Furthermore, because enhancement of the reaction by CDC was not confirmed with Control B, which was a substance similar to Sample B and rich in basic amino acids, it was also elucidated that the property of the peptide (basicity) did not necessarily affect the action of enhancing the reaction by CDC. On the basis of these results, it was found that the action of enhancing cytotoxic activity of antibody drug and complement was an action extremely specific to Sample A (lactoferrin hydrolysate mixture) or Sample B (lactoferrin partial peptide).

Preparation Example 3

Preparation of a Drug for Cancer Therapy Utilizing Lactoferrin Hydrolysate Mixture as Active Ingredient Lactose (Maigret, 600 g), maize starch (Nisshin Flour Milling Co., Ltd., 400 g), crystalline cellulose (Wako Pure Chemical Industries, 400 g) and the lactoferrin hydrolysate mixture produced in Preparation Example 1 (600 g) were sifted through a 50-mesh sieve (Yamato Scientific), placed in a polyethylene bag having a thickness of 0.5 mm, mixed by inversion and filled in capsules (Japan Elanco, gelatin capsule No. 1, Op. Yellow No. 6 Body, empty weight: 75 mg) in an amount of 275 mg/capsule by using a full automatic capsule filling machine (Cesere Pedini, press type) to obtain 7000 capsules of the drug having an effect of enhancing cytotoxic activity of antibody drug.

Preparation Example 4

Preparation of a Drug for Cancer Therapy Utilizing Lactoferrin Hydrolyzed Peptide as Active Ingredient Crystalline cellulose (Wako Pure Chemical Industries, 20 g) was placed in a 1000-ml volume mortar (Nakashima Mfg. Co., Ltd.), added with 20 ml of water and mixed. Then, to the mixture, 25 g of lactose (Maigret) sifted beforehand through a 48-mesh sieve (Wakamori) was added, and 55 g of the lactoferrin hydrolyzed peptide prepared in Preparation Example 2 was added and mixed. The obtained wet mass was placed on a 20-mesh sieve (Wakamori) and manually extruded onto a stainless steel plate for drying to prepare granules, and the granules were quickly and uniformly distributed, placed in a drier and dried at 25° C. for two days to obtain fine granules. These granules were sifted through a 20-mesh polyethylene sieve (Wakamori), and the granules passed through the sieve were spread on a large paper sheet, added with 2 g of magnesium stearate (Kanto Kagaku) sifted through a 48-mesh sieve beforehand and made uniform by manual mixing. The granules were made into tablets in a tablet making machine (Kimura Seisakusho, Model KT-2) using an R pestle having a diameter of 8 mm with setting compression pressure for the conditions of a tablet making number of 10, tablet weight of 6.2 g and Monsanto hardness of 3.5 to 5.0 kg to obtain 16 tablets of the drug having an effect of enhancing cytotoxic activity of antibody drug containing about 50% the lactoferrin hydrolyzed peptide.

INDUSTRIAL APPLICABILITY

Because the active ingredient of the drug for cancer therapy used in the present invention can be obtained from a comparatively inexpensive raw material such as cow's milk, it can be produced in a large scale. Furthermore, by enhancing cytotoxic activity of complement and antibody drug with the drug of the present invention, target tumor cells can be efficiently killed or injured. Furthermore, it also has an effect of recovering cytotoxic activity of complement and antibody drug for tumor cells having resistance to the antibody drug. That is, combined used of the drug of the present invention meets the request for continuously performing a therapy with an antibody drug even for a patient having recurrence of a malignant tumor having resistance to the antibody drug and judged that therapeutic treatment with the antibody drug is difficult. This evidently provides a novel guidepost for overcoming antibody drug resistance in cancer therapy.

What is claimed is:

1. A drug for an antibody therapy of cancer having resistance to the antibody drug, which comprises a lactoferrin hydrolysate obtainable by hydrolyzing lactoferrin with a hydrolytic enzyme, anti-CD20 antibody and complement, all of which are active ingredients.

2. The drug according to claim 1, wherein the hydrolytic enzyme is pepsin.

3. The drug according to claim 1, wherein degradation rate of the lactoferrin hydrolysate is 6 to 20%.

4. The drug according to claim 1, wherein the lactoferrin hydrolysate has a number average molecular weight of 500 to 5000.

5. A drug for an antibody therapy of cancer having resistance to the antibody drug, which comprises a peptide consisting of the amino acid sequence shown as SEQ ID NO: 2 and/or a peptide consisting of the amino acid sequence shown as SEQ ID NO: 3, anti-CD20 antibody and complement, all of which are active ingredients.

6. A method of treating cancer having resistance to an antibody drug comprising administering anti-CD20 antibody and complement and administering a lactoferrin hydrolysate obtainable by hydrolyzing lactoferrin with a hydrolytic enzyme in an amount sufficient to enhance a complement-dependent cytotoxic activity of the anti-CD20 antibody and/or the complement in an antibody therapy of cancer having resistance to the antibody drug to a subject in need thereof, wherein administration of the lactoferrin hydrolysate is before or after administration of the anti-CD20 antibody and/or complement or simultaneously with anti-CD20 antibody and/or complement.

7. A method for enhancing a complement-dependent cytotoxic activity of anti-CD20 antibody and/or complement in an antibody therapy of cancer having resistance to the antibody drug using anti-CD20 antibody and the complement, which comprises administering anti-CD20 antibody and complement and administering a lactoferrin hydrolysate obtainable by hydrolyzing lactoferrin with a hydrolytic enzyme to a patient in need thereof and which has an action of enhancing the complement-dependent cytotoxic activity of anti-CD20 antibody and/or the complement in an antibody therapy of cancer having resistance to the antibody drug, wherein the lactoferrin hydrolysate is administered before or after administration of anti-CD20 antibody and/or complement or simultaneously with anti-CD20 antibody and/or complement.

8. A method for enhancing a complement-dependent cytotoxic activity of anti-CD20 antibody and/or complement in an antibody therapy of cancer having resistance to the antibody drug using anti-CD20 antibody and the complement, which comprises administering anti-CD20 antibody and complement and administering a peptide consisting of the amino acid sequence shown as SEQ ID NO: 2 and/or a peptide consisting of the amino acid sequence shown as SEQ ID NO: 3 to a patient in need thereof wherein administration of the peptide(s) is before or after administration of anti-CD20 antibody and/or complement or simultaneously with anti CD20 antibody and/or complement.

* * * * *

SEQUENCE LISTING

```
<160> NUMBER OF SEQ ID NOS: 3

<210> SEQ ID NO 1
<211> LENGTH: 708
<212> TYPE: PRT
<213> ORGANISM: Bos taurus
<220> FEATURE:
<221> NAME/KEY: sig_peptide
<222> LOCATION: (1)...(19)
<223> OTHER INFORMATION: Lactoferrin

<400> SEQUENCE: 1

Met Lys Leu Phe Val Pro Ala Leu Leu Ser Leu Gly Ala Leu Gly Leu
1               5                   10                  15
```

-continued

```
Cys Leu Ala Ala Pro Arg Lys Asn Val Arg Trp Cys Thr Ile Ser Gln
             20                  25                  30

Pro Glu Trp Phe Lys Cys Arg Arg Trp Gln Trp Arg Met Lys Lys Leu
             35                  40                  45

Gly Ala Pro Ser Ile Thr Cys Val Arg Arg Ala Phe Ala Leu Glu Cys
 50                  55                  60

Ile Arg Ala Ile Ala Glu Lys Lys Ala Asp Ala Val Thr Leu Asp Gly
 65                  70                  75                  80

Gly Met Val Phe Glu Ala Gly Arg Asp Pro Tyr Lys Leu Arg Pro Val
                 85                  90                  95

Ala Ala Glu Ile Tyr Gly Thr Lys Glu Ser Pro Gln Thr His Tyr Tyr
                100                 105                 110

Ala Val Ala Val Val Lys Lys Gly Ser Asn Phe Gln Leu Asp Gln Leu
             115                 120                 125

Gln Gly Arg Lys Ser Cys His Thr Gly Leu Gly Arg Ser Ala Gly Trp
 130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
             180                 185                 190

Lys Gly Glu Gly Glu Asn Gln Cys Ala Cys Ser Ser Arg Glu Pro Tyr
                195                 200                 205

Phe Gly Tyr Ser Gly Ala Phe Lys Cys Leu Gln Asp Gly Ala Gly Asp
 210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
             260                 265                 270

Ala Val Val Ala Arg Ser Val Asp Gly Lys Glu Asp Leu Ile Trp Lys
             275                 280                 285

Leu Leu Ser Lys Ala Gln Glu Lys Phe Gly Lys Asn Lys Ser Arg Ser
 290                 295                 300

Phe Gln Leu Phe Gly Ser Pro Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
                340                 345                 350

Thr Ala Glu Glu Val Lys Ala Arg Tyr Thr Arg Val Val Trp Cys Ala
             355                 360                 365

Val Gly Pro Glu Glu Gln Lys Lys Cys Gln Gln Trp Ser Gln Gln Ser
             370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
                420                 425                 430

Asn Arg Lys Ser Ser Lys His Ser Ser Leu Asp Cys Val Leu Arg Pro
```

-continued

```
                435                 440                 445
Thr Glu Gly Tyr Leu Ala Val Ala Val Val Lys Lys Ala Asn Glu Gly
    450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
            500                 505                 510

Gly Ala Asp Pro Lys Ser Arg Leu Cys Ala Leu Cys Ala Gly Asp Asp
                515                 520                 525

Gln Gly Leu Asp Lys Cys Val Pro Asn Ser Lys Glu Lys Tyr Tyr Gly
    530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
            580                 585                 590

Leu Asp Gly Thr Arg Lys Pro Val Thr Glu Ala Gln Ser Cys His Leu
        595                 600                 605

Ala Val Ala Pro Asn His Ala Val Val Ser Arg Ser Asp Arg Ala Ala
    610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
            660                 665                 670

Arg Pro Thr Tyr Glu Glu Tyr Leu Gly Thr Glu Tyr Val Thr Ala Ile
        675                 680                 685

Ala Asn Leu Lys Lys Cys Ser Thr Ser Pro Leu Leu Glu Ala Cys Ala
    690                 695                 700

Phe Leu Thr Arg
705

<210> SEQ ID NO 2
<211> LENGTH: 25
<212> TYPE: PRT
<213> ORGANISM: Bos taurus

<400> SEQUENCE: 2

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 3
<211> LENGTH: 26
<212> TYPE: PRT
<213> ORGANISM: Bos taurus

<400> SEQUENCE: 3
```

-continued

```
Phe Lys Cys Arg Arg Trp Gln Trp Arg Met Lys Lys Leu Gly Ala Pro
1               5                   10                  15

Ser Ile Thr Cys Val Arg Arg Ala Phe Ala
            20              25
```